United States Patent [19]
Mohr et al.

[11] Patent Number: 6,133,489
[45] Date of Patent: Oct. 17, 2000

[54] OBTAINING GLYCOLS OF LOW ALDEHYDE CONTENT

[75] Inventors: Jürgen Mohr, Grünstadt, Germany; Frans Vansant, Kalmthout, Belgium

[73] Assignee: BASF Aktiengesellschaft, Ludwigshafen, Germany

[21] Appl. No.: 09/101,446
[22] PCT Filed: Jan. 21, 1997
[86] PCT No.: PCT/EP97/00271
 § 371 Date: Jul. 16, 1998
 § 102(e) Date: Jul. 16, 1998
[87] PCT Pub. No.: WO97/27164
 PCT Pub. Date: Jul. 31, 1997

[30] Foreign Application Priority Data

Jan. 22, 1996 [DE] Germany .......................... 196 02 116

[51] Int. Cl.$^7$ .......................... C07C 27/26; C07C 29/74; C07C 29/80; C07C 29/88
[52] U.S. Cl. .............................................. 568/914; 568/920
[58] Field of Search ................................... 568/914, 920; 528/274, 286, 287

[56] References Cited

FOREIGN PATENT DOCUMENTS 49-51212   5/1974   Japan .
49051212A  5/1974   Japan .

*Primary Examiner*—Joseph K. McKane
*Assistant Examiner*—Jane C. Osweck
*Attorney, Agent, or Firm*—Oblon, Spivak, McClelland, Maier & Neustadt, P.C.

[57] ABSTRACT

A process for obtaining glycols of low aldehyde content in which the plant used to obtain the glycol(s) is surface-treated, in whole or in part, with at least one reductive phosphorus compound.

12 Claims, 1 Drawing Sheet

OBTAINING GLYCOLS OF LOW ALDEHYDE CONTENT

This application is a 371 of PCT/EP97/00271 filed Jan. 21, 1997.

The present invention relates to a process for obtaining glycols of low aldehyde content and to products prepared using these glycols.

Glycols of low molecular mass, such as mono-, di- and triethylene glycol, are important products of the chemical industry. Monoethylene glycol in particular (also referred to as 1,2-ethanediol, ethylene glycol or simply MEG) is among the principal products of the chemical industry worldwide, and is used predominantly as antifreeze for vehicle radiators and as raw material for the production of polyesters.

The only process currently used for the large-scale industrial production of ethylene glycol comprises the hydrolysis of ethylene oxide and the subsequent working up of the resulting reaction mixture. Worldwide production capacity for ethylene glycol produced by ethylene oxide hydrolysis is currently estimated at $7 \times 10^6$ metric tons per annum. In this preparation process, the ethylene oxide is reacted continuously or in batches with water, in special reactors and under appropriate conditions. The resulting aqueous reaction mixture is then concentrated over several stages, and the crude glycol, finally, is purified by fractionation (cf. eg.: K. Weissermel, H.-J. Arpe, Industrielle Organische Chemie [Industrial Organic Chemistry], 3rd ed., VCH 1988, p. 159 ff.). The principal components of the reaction mixture are typically mono-, di- and triethylene glycol. Tetraethylene glycol and higher homologs are usually present in quantities so small that they are generally not worth recovering.

Distillation processes and apparatus for the purification of glycols, of various design, are known (cf. eg.: Ullmanns Encyklopädie der technischen Chemie [Ullmann's Encyclopedia of Industrial Chemistry], 4th edition, VCH 1974, Volume 8, p. 200 ff.). In the majority of cases, in serial distillation columns, first water and then ethylene glycol and, finally, the higher glycol ethers are recovered continuously. Various units can be used as evaporators for the distillations; modern continuous plants, however, employ falling-film evaporators for energy reasons. For reasons of cost, these plant components are commonly made from carbon steel.

Owing to the high boiling points of ethylene glycol and its homologs, the distillations always take place under reduced pressure. Any vacuum distillation unit, whether industrial-scale or laboratory-scale, possesses a certain leakage rate, ie. leaks which to a minor extent allow the surrounding atmosphere to enter the unit. Thus, in the course of operation, atmospheric oxygen finds its way into the vacuum distillation.

Like all alcohols, glycols can readily be oxidized both thermally (autoxidation) and catalytically. The reaction products of ethylene glycol with oxygen or other oxidizing agents are aldehydes (glycol aldehyde, glyoxal, formaldehyde, acetaldehyde) and the corresponding acids. On the other hand, however, especially when ethylene glycol is used to produce polyester films, there are particularly high purity requirements. Films produced using aldehyde-rich ethylene glycol prove to be highly sensitive to light. In particular, slight yellowing can be observed. Therefore, in the course of polyester production but also in other sectors, the presence of these oxidation products is extremely undesirable, so that the users are attempting to limit the aldehyde content by means of strict specification. For example, the aldehyde content of ethylene glycol intended for film production should be less than 20 ppm.

Provided no particular effects occur in the course of ethylene glycol production, the quantity of oxidation products formed is normally unimportant. However, it has been observed in industrial plants that a rise in the proportion of aldehyde in the distilled glycol may occur which was not readily explainable. At the same time, unusually large quantities of rust particles (magnetite) were found in the liquid phases of the distillation.

The problem set out above of increased aldehyde formation should also exist in the context of the distillative purification of ethylene glycol which has been prepared by other synthesis routes, for example the catalytic oxidation of ethylene in acetic acid.

Moreover, it is known that in large-scale industrial processes such as, for example, the manufacture of polyester fiber, large quantities of liquid, glycol-containing residues are produced. Recovery of the glycols present in these residues is reasonable from an economic standpoint. Finally, large quantities of ethylene glycol are produced in the form of used radiator fluid or used antifreeze, from which the glycol can likewise be recovered. In the distillative working up of these wastes, however, there is likewise the problem of unwanted aldehyde formation. A further factor is that the wastes may already contain small quantities of aldehyde, presenting an additional hindrance to the preparation of pure, ie. essentially aldehyde-free, glycols.

The term "glycol" as used herein embraces monoethylene glycol in particular and also the distillable homologs thereof, such as di-, tri- and tetraethylene glycol.

It is an object of the present invention, therefore, to provide a process which makes it possible to obtain glycols whose aldehyde content is markedly reduced. A particular object is to provide monoethylene glycol which reliably conforms to the strict specifications applying to starting materials for the production of polyester.

Surprisingly, we have found that this object is achieved by providing a process for obtaining glycols of low aldehyde content from glycol-containing mixtures, in which the plant used for the recovery of glycol is surface-treated, in whole or in part, with at least one reductive phosphorus compound. The intention is to treat at least those parts of the plant which come into contact with a glycol in the course of working up the mixture.

BRIEF DESCRIPTION OF THE DRAWINGS

The FIGURE shows a process scheme and apparatus components by which ethylene glycol is produced by an embodiment of the invention.

The surface treatment is intended in particular to be carried out on the inner faces of those parts of the plant which are permanently or temporarily in contact with a glycol in vapor form during the working up of the mixture. This applies in particular to plant components where processes are carried out at elevated temperature and to those produced from corrodable material, for example steel. This may be the case, for example, with evaporators and their feed and discharge pipes, distillation columns and reactors. In all of these plant components it is possible for vapor spaces to form in which the unwanted formation of aldehyde can take place at the temperatures prevailing therein.

Figure 1:
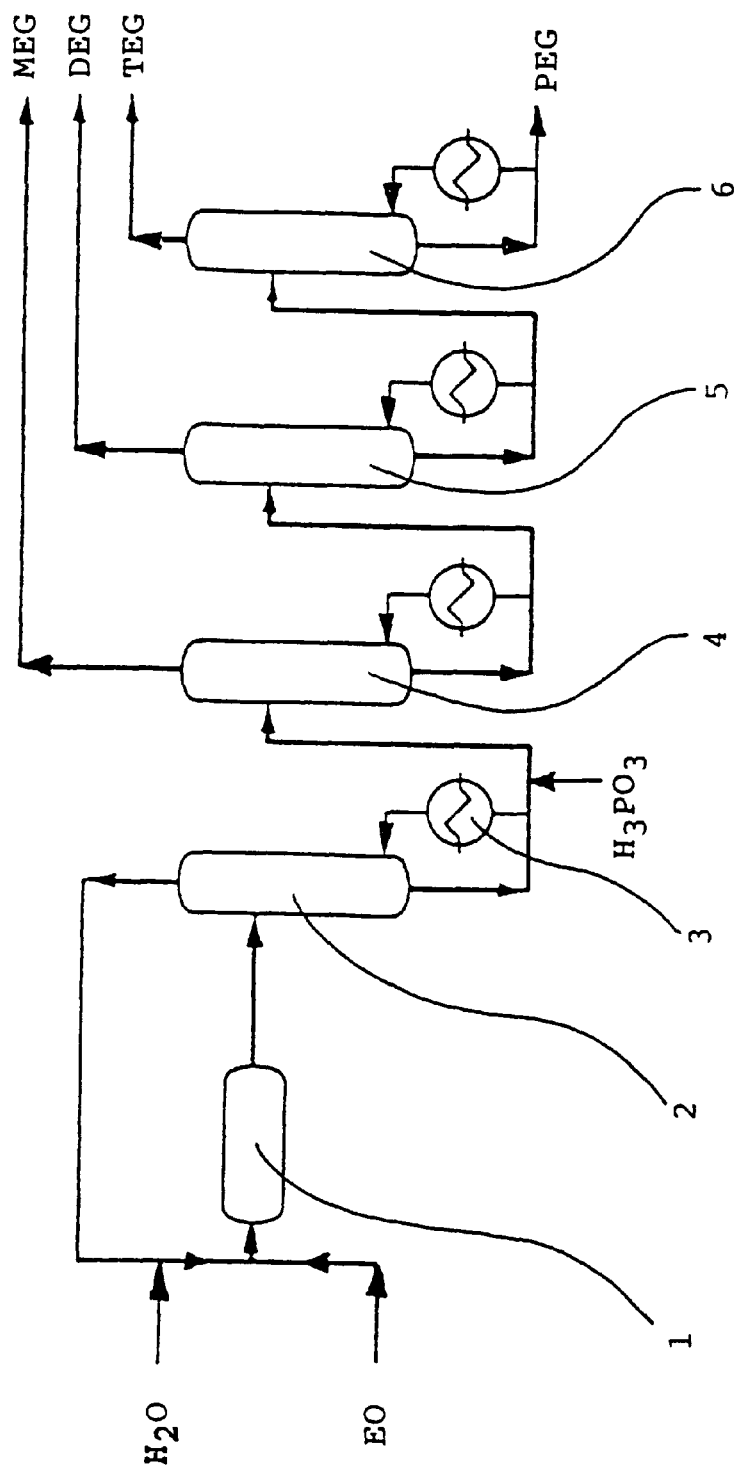

In accordance with the invention this surface treatment can be carried out discontinuously or continuously. In the case of a discontinuous procedure, the plant components required for separating the mixture can be treated, in whole or in part, with the phosphorus compound before the mixture is processed, for example, the distillation column used for the vacuum distillation of monoethylene glycol can be treated with the phosphorus compound if monoethylene glycol low in aldehyde is to be produced. For the discontinuous procedure, the surface treatment can be carried out, for example, before processing each batch of mixture to be worked up, or else at other appropriate intervals of time. This is dependent on the severity of the reformation of aldehyde which is observed in the case of separation.

If, on the other hand, operation is continuous, then the phosphorus compound can be added to the glycol-containing mixture prior to separation. The phosphorus-containing mixture can then be separated in the plant. In accordance with the invention it is particularly preferred to meter the phosphorus compound into the mixture continuously, directly before separation. This is particularly advisable if it is expected that the mixture to be separated contains aldehyde even before separation. By this means it is possible to reduce these aldehydes by means of the phosphorus compound even before the actual separation step. If it is desired, for example, to prepare monoethylene glycol low in aldehyde, then the phosphorus compound can be added continuously, directly before introduction into the vacuum distillation column which is used for monoethylene glycol separation, to a glycol-containing mixture produced, for example, by continuous hydrolysis of ethylene oxide.

A combination of continuous and discontinuous procedure is likewise conceivable.

The phosphorus compound used in accordance with the invention may be any organic or inorganic phosphorus compound or a combination of organic and inorganic phosphorus compounds showing the desired reductive effect. The phosphorus compound applied comprises a reductive $p^{+3}$-containing species. Preferably it is chosen from phosphorous acid (which is predominantly in the stable tautomeric form $HP(O)(OH)_2$, which is also called phosphonic acid; cf. Römpp Chemie Lexikon [Römpp's Chemical Dictionary], 9th ed.) and the salts thereof. Salts of phosphorous acid are preferably selected from water-soluble salts such as, in particular, alkali metal phosphites, zinc phosphites and calcium phosphites. Particularly preferred alkali metal phosphites are sodium phosphite and potassium phosphite. The corresponding hydrogen phosphites can also be used. What is most preferred, however, is to use the acid itself.

If the phosphorus compound is added to the mixture itself, this addition is usually made such that the phosphorus compound is present in a proportion of from about 10 to about 5000 ppm before glycol is removed from the mixture. The proportion should preferably be in the range from about 100 to about 1000 ppm, and should in particular be about 500 ppm. The phosphorus compound is preferably added as a solution in a glycol, such as monoethylene glycol.

If the plant is to be surface-treated discontinuously with the phosphorus compound, then a solution is prepared containing the phosphorus compound in a proportion of about 0.1 to 10% by weight, preferably from about 0.5 to 5% by weight, based on the overall weight of the solution. The phosphorus compound can be dissolved in a suitable organic solvent, for example monoethylene glycol, or in an aqueous solvent, for example water. An aqueous solution is preferably used. The solution prepared in this way is then used to treat those parts of the plant which are required for separating the mixture. Treatment can be carried out, for example, by flooding the relevant parts of the plant with the solution and incubating them for a suitable period. An alternative possibility would be flushing of the parts of the plant, allowing the solution to circulate for an appropriate period by pumping it around the plant parts. Also conceivable is spraying or irrigation of the parts of the plant. The necessary treatment period can be determined by the skilled worker without great difficulty, and may, for example, be from about 2 to 8 hours, for instance 4 to 6 hours. Treatment can be carried out at ambient temperatures or, for example, with heated aqueous solution (heated for example at 40–80° C.).

Working up of the glycol-containing mixture in accordance with the invention produces, in particular, ethylene glycol of surprisingly low aldehyde content, the latter being in the region of less than about 20 ppm, for example about 10–20 ppm. Surprisingly, the novel process makes it possible to conform reliably to the strict specifications for ethylene glycol as apply, in particular, to the production of polyester fibers and films.

Without being limited to the following explanation, the surprising effect observed in accordance with the invention can be explained as follows:

The autoxidation of ethylene glycol, ie. the direct reaction with oxygen without a catalyst, is a slow process. In laboratory experiments where glycol is subjected, under the conditions of a typical vacuum distillation, to the oxygen which penetrates as a result of the natural leakage rate, only a slow and small increase in the aldehyde levels is observed. This is particularly the case when these experiments are carried out in apparatus made of inert materials (e.g. glass). Even artificial leakage rates involving increased supply of oxygen lead to no drastic worsening of these levels.

If, however, iron bodies (eg. filings) are introduced into the same experimental setup in such a way that they are able to come into contact with the vapor phase over the distilled glycol, then, at an identical leakage rate, aldehyde contents increased by a multiple are observed. At the same time, corrosion occurs to a certain extent on the iron surfaces, forming primarily magnetite (rust).

Even with pure magnetite instead of iron filings, the same increased formation of aldehyde is observed. However, if iron filings or magnetite are in liquid (for example in the liquid distillation phase), so that no gas-phase contact is possible, then the increased formation of aldehyde is also absent.

The formation of magnetite as a protective coating in plant components made of iron is known per se and is indeed desirable. Under certain circumstances, however, particles may be detached from a compact magnetite coating and, having passed to another part of the plant, catalytically promote the oxidation of glycol. Indeed, such magnetite particles may occasionally be isolated by filtration in small quantities in the course of processes which are in operation. If these particles arise continuously, then the plant must be protected against corrosion by another means.

By the novel addition of phosphorous acid and/or phosphites to the feed streams of the distillations it is possible to prevent both corrosion, with formation of magnetite, and the unwanted oxidation of glycol.

The present invention is now illustrated in more detail with reference to the following working examples.

WORKING EXAMPLES

Using the experiments described in Examples 1 to 4, the effect of the plant material on the formation of aldehyde from ethylene glycol was investigated:

Example 1

Distillation Experiments with Ethylene Glycol

Ethylene glycol (700–800 ml) was first of all distilled at 200 mbar and a liquid-phase temperature of 150–160° C. in a simple distillation apparatus consisting of distillation boiler with boiling capillary, packed column (l=40 cm; d=2.5 cm), descending condenser, receiver and device for producing reduced pressure. 13% liquid phase was allowed; the duration of the experiment was about 2 h. Glass rings or iron rings were used as packing for the column. Either air or nitrogen was bubbled in via the boiling capillary.

The results are compiled in Table 1 below:

TABLE 1

Distillation of glycol over glass or iron packing

| | | Packing | | | |
|---|---|---|---|---|---|
| | | Glass | | Iron | |
| | | Aldehyde (ppm)[1) 3)] | | | |
| Conditions: | | free | total[2)] | free | total[2)] |
| Air | Distillate | 27 | 38 | 42 | 53 |
| | Liquid phase | <5 | 51 | 30 | 55 |
| | Balance | 24 | 40 | 40 | 53 |
| Nitrogen | Distillate | 14 | 25 | 24 | 30 |
| | Liquid phase | <5 | 57 | 12 | 52 |
| | Balance | 13 | 29 | 22 | 33 |

[1)]Initial aldehyde levels: free = 15 ppm; total = 22 ppm
[2)]The difference between free aldehyde and total aldehyde is the so-called bound aldehyde which in the present case, especially in the form of the acetals, escapes direct determination.
[3)]The aldehyde levels were determined in accordance with the MBTH method, a photometric method for free and bound aldehyde (similar to E. Savicky et al., Analyt. Chem., 33, (1961), 93–96).

The overall aldehyde contents which are balanced (ie. obtained taking into account the liquid phase: distillate ratio of 13:87) from the table are particularly important for interpreting the analytical data.

In the presence of air, an increase in the total aldehyde content is observed which, however, is much greater in the case of the iron packing. Moreover, on this packing a granular, readily movable black magnetite coating is formed.

If the distillation is carried out under nitrogen, the formation of aldehyde is substantially smaller to virtually negligible.

Example 2

Reflux Experiments

In further experiments, glycol was heated under reflux, ie. without distillative removal, in the apparatus according to Example 1 and under otherwise largely identical conditions in this way, contact between vapor space and the material being investigated can be maintained over a longer period, so that the posited effects are able to occur to a greater extent.

The column was operated either as a pure glass column (empty) or filled with iron filings. The latter experimental setup simulates a reflux condenser of iron or a corresponding evaporator with gas-phase contact.

The results are compiled in Table 2.

TABLE 2

Refluxing of glycol in the presence of iron packing in the gas phase

| Experiment No. | Time (h) | Atmosphere | Aldehyde[1) 3)] [ppm] |
|---|---|---|---|
| 1 | 13 | Air | 162 |
| 2 | 14 | Air | 180 |
| 3 | 12 | Nitrogen | 40 |
| 4[2)] | 20 | Air | 38 |

[1)]Total aldehyde
[2)]Control experiment in glass
[3)]Initial aldehyde level 23 ppm It is observed that, with the ingress of air at the iron surface, ethylene glycol forms a large quantity of aldehyde in a relatively short time.

Comparison in particular with the blank experiment (No. 4), which despite a prolonged running time (20 hours) shows an increase in the aldehyde content by only 15 ppm, makes clear the connection between aldehyde formation and iron surface. In the course of the experiments in the presence of oxygen, the iron surface becomes covered with a dark oxide layer.

Example 3

Refluxing in the Immersed Phase

Pure monoethylene glycol (MEG) was refluxed in a glass apparatus according to Example 1 (p=200 mbar; T=150–160° C.). Iron filings were placed in the liquid phase, entirely immersed, and were therefore unable to come into contact with the gas phase. Air was again bubbled in via the boiling capillary. Table 3 shows the measured total aldehyde levels at the end of the experiments.

TABLE 3

Refluxing of glycol in the presence of iron packings in immersed phase

| No. | Material | Atmosphere | Aldehyde[1)] [ppm] |
|---|---|---|---|
| 1 | Glass | Air | 38 |
| 2 | Glass + iron (immersed) | Air | 39 |

[1)]Initial levels 23 ppm

Accordingly, iron in immersed phase shows the same behavior as the empty glass apparatus; the increased formation of aldehyde in the previous experiments must therefore take place in the gas phase.

Example 4

Pretreatment with Phosphorous Acid

In two parallel experiments, a glass column was filled with the following packings:

(1) untreated filings
(2) filings which had been stored overnight beforehand in a 1% strength solution of phosphorous acid in glycol.

The experimental procedure was as in Example 2.

The results are compiled in Table 4.

TABLE 4

Effect of pretreating the packing with phosphorous acid

| No. | Treatment | Duration [h] | Total aldehyde [ppm][1) |
|---|---|---|---|
| 1 | / | 13 | 162 |
| 2 | $H_3PO_3$ | 45 | 40 |

[1)]Initial levels 23 ppm

With the ingress of air, aldehyde is produced in the case of the untreated iron filings, with the simultaneous formation and deposition of magnetite.

In the case of the treated iron filings, this corrosion occurs virtually not at all and the liquid phase remains almost clear.

The proportion of re-formed aldehyde is substantially lower than in the first case.

In the case of treatment with phosphorous acid, the filings become coated with a green covering which is retained over the duration of the experiment.

Example 5

Operational Experiment

An operational experiment was carried out in a continuous production plant which operates essentially in accordance with the scheme shown in the attached FIGURE. After $H_2O$ and ethylene oxide (EO) have been reacted in the reactor (1) and the crude product has been dewatered in the drying column (2), phosphorous acid (dissolved in monoethylene glycol) at a concentration of 20 ppm is metered in continuously to the ethylene glycol mixture after it has passed through the evaporator (3) and before it enters the distillation column (4). A marked reduction in the total aldehyde content in the pure monoethylene glycol (MEG) is observed (cf. Table 5).

TABLE 5

Reduction in the total aldehyde content in monoethylene glycol prepared on the industrial scale

| Aldehyde in the Reaction mixture | Aldehyde in MEG fraction | Equilibrium after |
|---|---|---|
| 10–30 ppm | <10 ppm | 2 hours |

At the same time, there is also a reduction in the amount of rust or magnetite which can be removed by filtration from the liquid-phase discharge of the distillation.

If desired, $H_3PO_3$ can also be metered in directly before the distillation columns (5) and (6), should the preparation of diethylene glycol (DEG) or triethylene glycol (TEG) of low aldehyde content be required.

We claim:

1. A process for obtaining glycols with low aldehyde content from a glycol-containing mixture, which comprises:

treating the surfaces of apparatus component made from corrodible material of a plant assembled for glycol recovery with phosphorous acid or a salt thereof, wherein the phosphorous acid or a salt thereof is added to glycol-containing mixture before or during the working-up of said mixture;

subsequently recovering the glycol(s) by distillation; and optionally further pre-treating said plant used for the working-up of said mixture, in whole or in part, with said phosphorous acid or a salt thereof, wherein said surface treatment discontinuously takes place at least in those apparatus components of the plant which, permanently or temporarily, are in contact with a glycol in vapor form in the course of work-up of the glycol product.

2. The process as claimed in claim 1, wherein the phosphorus compound is metered continuously into the glycol-containing mixture in an amount of about 10 to about 5000 ppm, mixing is conducted, if desired, and then the glycol(s) is(are) separated from the mixture.

3. The process as claimed in claim 1, wherein the apparatus components of the plant are discontinuously pretreated, in whole or in part, with a solution which contains the phosphorus compound in an amount of about 0.1 to about 10% by weight.

4. The process as claimed in claim 1, wherein the apparatus components of the plant are discontinuously pretreated, in whole or in part, with a solution which contains the phosphorus compound in an amount of about 0.1 to about 10% by weight.

5. The process as claimed in claim 3, wherein the apparatus components of the plant, in whole or in part, is flushed, flooded, irrigated or sprayed with the solution.

6. The process as claimed in claim 4, wherein the apparatus components of the plant, in whole or in part, are flushed, flooded, irrigated or sprayed with the solution.

7. A process for obtaining glycols with low aldehyde content from a glycol-containing mixture, which comprises:

treating the surfaces of apparatus component made from corrodible material of a plant assembled for glycol recovery with phosphorous acid or a salt thereof, wherein the phosphorous acid or a salt thereof is added to glycol-containing mixture before or during the working-up of said mixture;

subsequently the glycol(s) by distillation; and optionally further pre-treating said plant used for the working-up of said mixture, in whole or in part, with said phosphorous acid or a salt thereof.

8. The process as claimed in claim 7, wherein the salt of a phosphorus acid is a water-soluble salt selected from the group consisting of an alkali metal phosphite, calcium phosphite and zinc phosphite.

9. The process as claimed in claim 1, wherein the glycol-containing mixture to be processed is a reaction mixture obtained from the production of ethylene glycol.

10. The process as claimed in claim 1, wherein the glycol-containing mixture to be processed is selected from the group consisting of liquid wastes and residues from chemical production.

11. The process as claimed in claim 10, wherein the liquid waste is selected from the group consisting of used radiator fluid and antifreeze liquids.

12. The process as claimed in claim 1, wherein the glycol obtained is monoethylene glycol, diethylene glycol, triethylene glycol or mixtures thereof, each of a low aldehyde content.

* * * * *